United States Patent [19]

Christain et al.

[11] Patent Number: 4,907,332
[45] Date of Patent: Mar. 13, 1990

[54] DEVICE FOR CONNECTING EXTENDABLE GUIDEWIRE SECTIONS FOR CARDIOVASCULAR PROCEDURES

[75] Inventors: Jeffrey J. Christian, San Jose; Ross Gould, Berkeley; Isidro Gandionco, Fremont, all of Calif.

[73] Assignee: Advanced Cardiovascular Systems, Inc., Mountain View, Calif.

[21] Appl. No.: 142,070

[22] Filed: Jan. 11, 1988

[51] Int. Cl.⁴ ............................................. B23P 19/04
[52] U.S. Cl. ........................................ 29/237; 29/238; 604/905; 128/657
[58] Field of Search ............... 128/330 R, 334, 657, 128/772; 604/95, 165, 164, 170, 171, 905; 29/237, 238, 234, 235, 467; 140/111, 113, 116, 151

[56] References Cited

U.S. PATENT DOCUMENTS

| | | | |
|---|---|---|---|
| 4,149,534 | 4/1979 | Tenczar | 604/905 |
| 4,402,682 | 9/1983 | Garver, Sr. et al. | 604/905 |
| 4,402,691 | 9/1983 | Rodenthal et al. | 604/905 |
| 4,687,470 | 8/1987 | Okada | 128/657 |
| 4,726,369 | 2/1988 | Mar | 128/657 |

Primary Examiner—Mark Rosenbaum
Assistant Examiner—Peter Vo
Attorney, Agent, or Firm—Fulwider, Patton, Lee & Utecht

[57] ABSTRACT

A device to facilitate the joining of a male proximal end of a guidewire to the female end of an extension wire. The device has a relatively flat body with a guiding groove in the upper surface with two aligned sections, the goove sections tapering inwardly toward the intersection thereof. One of the groove sections is adapted to receive the male end of the guidewire and one groove is adapted to receive the female end of the extension. One, preferably two, flexible tabs are secured to the upper surface of the body to maintain one of the ends within its respective groove section. The device and/or the connecting wires can be disengaged by the rotation thereof with respect to each other.

8 Claims, 1 Drawing Sheet

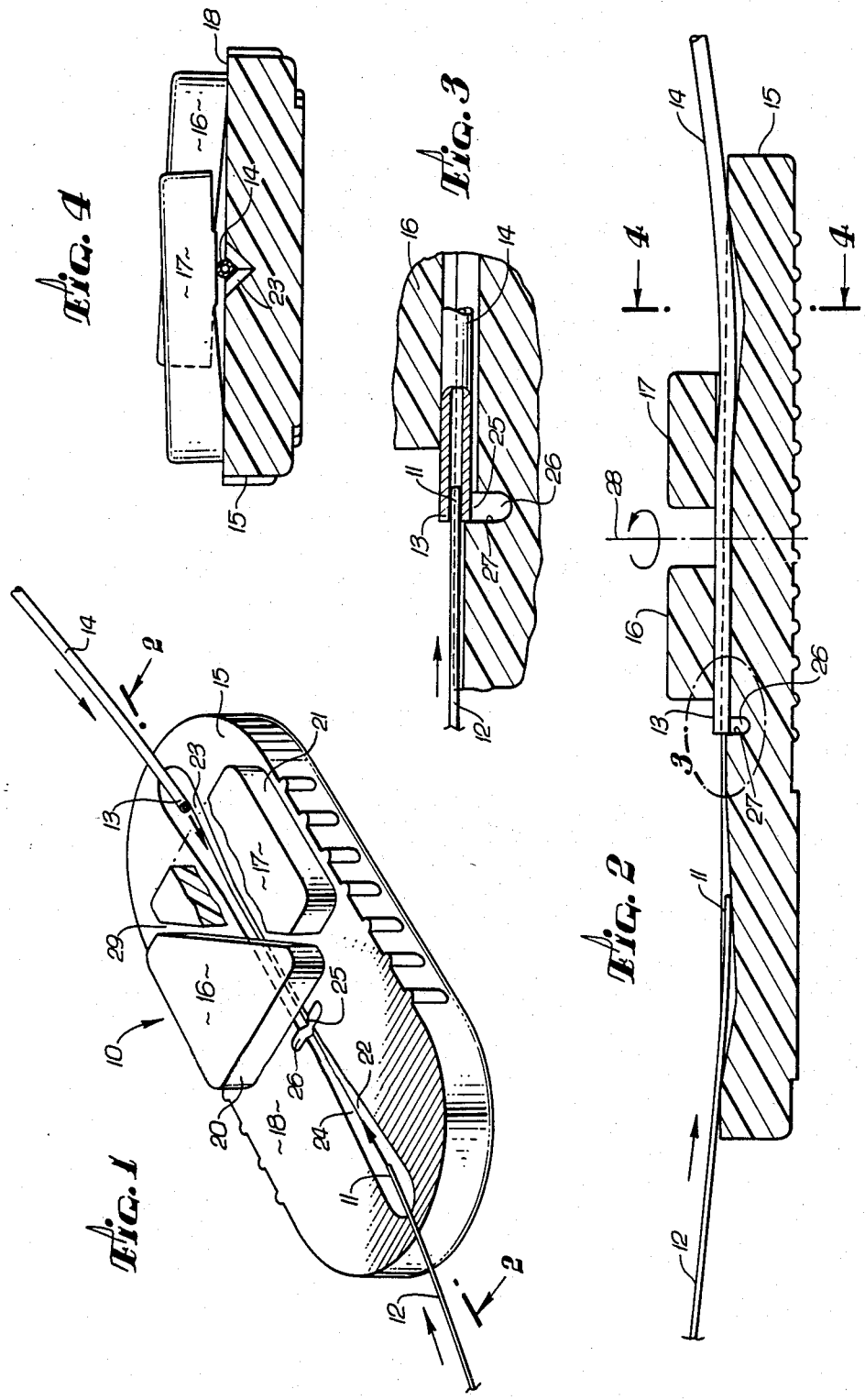

DEVICE FOR CONNECTING EXTENDABLE GUIDEWIRE SECTIONS FOR CARDIOVASCULAR PROCEDURES

BACKGROUND OF THE INVENTION

This invention generally relates to cardiovascular procedures such as angioplasty, angiography and valvuloplasty, and more particularly to the connection of guidewire extensions for use in such procedures.

Guidewires are currently used to facilitate the placement of catheters in the arterial system of a patient for cardiovascular procedures. The guidewire is typically on the order of 20-50 cm longer than the catheter to permit the guidewire and the catheter to be advanced relative to each other as they are steered into position within the patient's body. Suitable guidewires are described in U.S. Pat. Nos. 4,538,622 (Samson et al.); 4,554,929 (Samson); and 4,569,347 (Frisbie) which are hereby incorporated herein in their entirety.

In a typical procedure to change catheters, the guidewire is removed from the patient, and an exchange wire is inserted in its place. The in-place catheter is removed from the patient and a new catheter is inserted into the patient over the exchange wire. The exchange wire is then removed from the patient and the guidewire is reinserted. The exchange wire is substantially longer than the guidewire, and it generally extends outside the patient's body for a distance greater than the length of the catheter to facilitate the catheter exchange. With a dilation catheter having a length on the order of 120-140 cm, for example, a guidewire might have a length on the order of 175 cm, and an exchange wire might have a length on the order of 300 cm. The use of an exchange wire has the obvious disadvantage that it complicates the angioplasty procedure.

Copending application Ser. No. 137,963, now Pat. No. 4,827,941 filed Dec. 23, 1987, by Taylor et al. and assigned to the present assignee described means to eliminate the need for an exchange wire by attaching an extension wire to an in-place guidewire to extend the length thereof whenever a catheter is to be exchanged. As described herein, the two wires are joined together by a female tubular element on the end of one of the sections and a male element on the end of the other section which is releasably secured within the tubular element. The aforesaid copending application is hereby incorporated herein in its entirety.

While an improved guidewire system is described in the aforesaid copending application, the tubular element and the male interfitting element of the guidewire and extension have very small diameters which makes the manual insertion of the interfitting element into the tubular element very difficult, particularly in the conditions in which the cardiovascular procedures are conducted.

SUMMARY OF THE INVENTION

The present invention is directed to a device which facilitates the connecting of an end of a guidewire to an end of an extension wire wherein one of the ends to be connected has a tubular female element and the other end has a male element adapted to be inserted into the tubular female element and releasably secured therein.

The device in accordance with the present invention generally has a base member with an elongated guide means or groove in the upper portion thereof having two integral guide sections which taper inwardly toward the intersection of the two groove sections. One of the tapered sections is adapted to slidably receive the female element and one tapered section adapted to slidably receive the male element. At least one, preferably two, tabs are secured to the upper surface of the base member and extend across a guiding groove section to ensure that one of the connecting elements is held within the groove during the connection with the other element.

In one preferred embodiment, one of the tabs is secured to the base member on one side of the guiding groove and the other tab is secured to the base member on the other side of the guiding groove. The facing edges of the tabs are preferably spaced from one another and form a linear or slotted opening which is at an angle from the guiding groove to facilitate removal of the joined guidewire sections after the interconnection thereof.

The proximal end of the guidewire and the distal end of an extension wire having a female tubular element thereon are slidably moved inwardly along the appropriate guiding groove section until the male element is properly disposed within the tubular female element where it is releasably secured. The connecting device can then be removed from the connected elongated members by the relative rotation thereof with respect to the connected elongated members so that they can pass through the slotted opening between the tabs which is an an angle with the guiding groove.

The connection betweeen a guidewire an an extension wire can be made easily and quickly under conditions normally found in percutaneous transluminal cardiovascular procedures with the device of the invention. These and other advantages of the invention will become more apparent from the following detailed description thereof and the accompanying exemplary drawings.

BRIEF DESCRIPTION OF THE DRAWINGS

FIG. 1 is a perspective view of a connecting device embodying features of the invention;

FIG. 2 is a cross-sectional view taken along the lines 2—2 shown in FIG. 1;

FIG. 3 is an enlarged sectional view shown by the circle 3—3 in FIG. 2; and

FIG. 4 is an end elevational view partially in section of the device shown in FIG. 1 taken along the lines 4—4 as shown in FIG. 2.

DETAILED DESCRIPTION OF THE INVENTION

Reference is made to FIG. 1 which illustrates a connecting device 10 for joining the proximal male end 11 of a guidewire 12 and the distal female end 13 of an extension wire 14 to facilitate catheter exchange during cardiovascular procedures.

With particular reference to the drawings, the connecting device 10 generally comprises a body 15 and flexible tabs 16 and 17 secured to the upper surface 18 of the body 15. Preferably, as shown in the drawings, the triangular-shaped tabs 16 and 17 are secured by their bases 20 and 21 on opposite sides of guiding groove 22. The guiding groove 22 has two aligned sections 23 and 24 both of which taper inwardly toward the intersection 25 thereof. Groove section 23 is adapted to slidably receive and guide a tubular female end 13 of an extension wire 14, and groove section 24 is adapted to slidably receive and guide the male end 11 of the guidewire 12 toward the female end 13 in groove section 23.

The intersection 25 between the groove sections 22 and 23 is best shown in the enlarged cross-sectional view shown in FIG. 3, illustrating the partial insertion of the end 11 into the tubular end 13. The groove section 23 positions the female end 13 of the extension wire 14 to ensure the proper reception of the male end 11 of the guidewire 12. The flexible tabs 16 and 17 press the extension wire 14 into the groove to ensure its alignment. A transverse channel 26 is provided at the intersection 25 to form a vertical wall 27 which acts as a stop to impede the movement of the female end 13, which is usually inserted first along groove section 23. Generally, at the intersection 25 of the groove sections 23 and 24, the cross-sectional dimension of the groove section 23 adapted to receive the tubular element 13 is larger than the corresponding cross-sectional area of the groove section 24 for the male element 11. The groove sections, which are preferably V-shaped in cross section, are aligned so that the female end 23 and male end 24 are coaxially aligned prior to connection.

A preferred mode of using the connecting device 10 comprises first inserting the female end 13 of the extension wire 14 into the groove 23 until the distal tip thereof contacts the vertical wall 27 impeding further movement. The connecting device 10 with the female element 13 appropriately positioned in the groove section 23 is then directed toward the male end 11 of the guidewire 12. The male end 11 is manually urged into the groove section 24 with one hand, and the connecting device 10, with the female end 13 of the extension wire 14 properly positioned within groove 23, is manually urged toward the male end of the guidewire 12 to thereby insert the male end 11 into the female tubular end 13 to be releasably secured therein. Once the elongated members 12 and 14 are joined, the connecting device 10 may be rotated so that relative to the joined wires about an axis 28 normal to the groove 22 they are aligned with the linear or slotted opening 29 between the facing edges or tabs 16 and 17 and can then be readily removed from device 10.

While the presently preferred embodiment of the connecting device 10 has been described herein whereby the tabs 16 and 17 are positioned to extend over groove section 23 which is adapted to receive the female end 13 of the exchange wire 14, the tabs could very readily be disposed to extend over groove section 24 which is adapted to receive the male member 11. Moreover, while the wire extension 14 is described herein as having distal tubular end 13 and the guidewire 12 is described as having proximal male end 11, these ends could be reversed, i.e., the guidewire having a female proximal end and the extension wire having a male distal end.

The body member 10 can be made of suitable material such as plastic, metal, and the like. However, plastic is preferred because of the cost and the ease of the high volume manufacture thereof. The tabs 16 and 17 are preferably flexible and formed of rubber or other elastomers. Other modifications and improvements can be made to the invention without departing from the scope thereof.

What is claimed is:

1. A device for vascular procedures to facilitate the interconnection of a first elongated hollow member having an open female end and a second elongated hollow member having a male end comprising:
   (a) a body member having an upper portion with an elongated guiding groove therein having first and second groove sections, said groove sections tapering inwardly toward a location where said sections intersect, one of the sections adapted to slidably receive the female end of the first elongated member and the second section adapted to slidably receive the male end of the second elongated member, said groove sections cooperating to guide the female end and the male end into engagement; and
   (b) two flexible tabs longitudinally spaced along guiding grooves with one tab secured to the upper portion of the body member at one end thereof on one side of the guiding groove and extending over the elongated guiding groove and a second tab secured to the upper portion of the body member at one end thereof on the other side of the guiding groove section and extending over said elongated guiding groove to hold an end of the elongated members within the grooves.

2. The device of claim 1 wherein facing edges of the two tabs form an opened slot therebetween at an angle with the elongated guiding groove to facilitate the disengagement of connected elongated members from the device.

3. The device of claim 1 wherein the groove sections are aligned so that when the female end and the male end are moved along their respective groove sections, they are in proper registry for engagement.

4. The device of claim 1 wherein the flexible tabs are triangularly shaped and the base thereof is secured to the upper portion of the base member.

5. The device of claim 1 wherein the flexible tabs are formed of natural rubber or elastomeric materials.

6. The device of claim 1 wherein the groove section adapted to receive the female end of the first elongated member has a larger cross section at the location where said sections intersect than the groove section adapted to receive the male end of the second elongated member at said location.

7. The device of claim 1 wherein the first groove section adapted to receive the female end on the first elongated member is provided with a stop to properly position the female end to facilitate the insertion of the male end of the second elongated member therein.

8. The device of claim 7 wherein the stop is provided at the intersection of the groove sections to impede the movement of the female end of the first elongated member along the groove section adapted to receive same.

* * * * *